(12) United States Patent
Yamagami et al.

(10) Patent No.: US 10,007,659 B2
(45) Date of Patent: Jun. 26, 2018

(54) METHOD FOR ASSIGNING SEMANTIC INFORMATION TO WORD THROUGH LEARNING USING TEXT CORPUS

(71) Applicant: Panasonic Intellectual Property Management Co., Ltd., Osaka (JP)

(72) Inventors: Katsuyoshi Yamagami, Osaka (JP); Takashi Ushio, Osaka (JP); Yasunori Ishii, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days. days.

(21) Appl. No.: 15/176,114

(22) Filed: Jun. 7, 2016

(65) Prior Publication Data

US 2016/0371254 A1  Dec. 22, 2016

(30) Foreign Application Priority Data

Jun. 17, 2015  (JP) .................................. 2015-121670

(51) Int. Cl.
*G06F 17/28* (2006.01)
*G10L 15/00* (2013.01)
(Continued)

(52) U.S. Cl.
CPC ...... *G06F 17/2785* (2013.01); *G06F 17/2795* (2013.01); *G06F 19/36* (2013.01); *G06N 3/0472* (2013.01); *G06N 3/08* (2013.01)

(58) Field of Classification Search
CPC .. G06F 17/2785; G06F 17/2795; G06F 19/36; G06F 17/274; G06F 17/275;
(Continued)

(56) References Cited

U.S. PATENT DOCUMENTS 5,371,807 A * 12/1994 Register ............ G06F 17/30707
  382/159
7,181,451 B2 * 2/2007 Dehlinger ............... G06F 17/27
(Continued)

FOREIGN PATENT DOCUMENTS

JP  2002-334077  11/2002

OTHER PUBLICATIONS

The Extended European Search Report dated Nov. 22, 2016 for the related European Patent Application No. 16172676.5.
(Continued)

*Primary Examiner* — Chan S Park
*Assistant Examiner* — Stephen M Brinich
(74) *Attorney, Agent, or Firm* — Greenblum & Bernstein, P.L.C.

(57) ABSTRACT

A method includes acquiring a first corpus, including first text of a first sentence including a first word and described in a natural language, and second text of a second sentence including a second word different in meaning from the first word, a second word distribution of the second word being similar to a first word distribution of the first word, acquiring a second corpus including third text of a third sentence, including a third word identical to the first word and/or the second word, a third word distribution of the third word being not similar to the first word distribution, based on an arrangement of a word string in the first corpus and the second corpus, assigning to the first word a first vector representing a meaning of the first word and assigning to the second word a second vector representing a meaning of the second word.

16 Claims, 10 Drawing Sheets

(51) Int. Cl.
*G06F 17/27* (2006.01)
*G06F 19/00* (2018.01)
*G06N 3/04* (2006.01)
*G06N 3/08* (2006.01)

(58) Field of Classification Search
CPC ...... G06F 17/278; G06F 17/279; G06F 17/28; G06N 3/0472; G06N 3/08; G06N 3/0427; G06N 3/0436; G06N 3/0463; G06N 3/049; G06N 3/082; G06N 3/084; G06N 3/086; G06N 3/0868; G06N 3/0863
USPC ........................ 704/1–10, 251–259, E15.024
See application file for complete search history.

(56) References Cited

U.S. PATENT DOCUMENTS

| | | | |
|---|---|---|---|
| 2004/0078190 A1* | 4/2004 | Fass | G06F 17/241 704/7 |
| 2005/0004790 A1* | 1/2005 | Wu | G06F 17/2715 704/9 |
| 2008/0077396 A1* | 3/2008 | Hsu | G06F 17/273 704/10 |
| 2011/0257961 A1* | 10/2011 | Tinkler | G09B 19/04 704/9 |
| 2013/0024183 A1* | 1/2013 | Cardie | G06F 17/30719 704/8 |
| 2013/0149681 A1* | 6/2013 | Tinkler | G09B 19/00 434/167 |

OTHER PUBLICATIONS

Enrico Santus et al: "Unsupervised Antonym-Synonym Discrimination in Vector Space", Proceedings of the First Italian Conference on Computational Linguistics (CLIC-IT 2014), Dec. 10, 2014 (Dec. 10, 2014), XP055318531, Pisa DOI: 10.12871/CLICIT2014163.
Tomohide Shibata et al., "Context-dependent Synonymous Predicate Acquisition", Information Processing Society of Japan, vol. 2010-NL-199 No. 13, 2010.
Tomas Mikolov et al., "Efficient Estimation of Word Representations in Vector Space", ICLR 2013.
Tomas Mikolov et al., "Distributed Representations of Words and Phrases and their Compositionality", NIPS 2013.

* cited by examiner

| ID | W1 | W2 | W3 | W4 | W5 | W6 | ... |
|---|---|---|---|---|---|---|---|
| ... | | | | | | | |
| 0011 | NIPPON | NO | JINKO | WA | HERI | MASU | |
| 0012 | CHUGOKU | KARANO | RAINICHI | GA | FUE | TA | |
| 0013 | PETTO | WO | KAU | HITO | GA | OOI | |
| 0014 | TEREBI | DE | SAKKA- | WO | MIRU | | |
| ... | | | | | | | |

201B

| ID | W1 | W2 | W3 | W4 | W5 | ... |
|---|---|---|---|---|---|---|
| ... | | | | | | |
| 0011 | JAPANESE | POPULATION | IS | DECREASING | | |
| 0012 | CHINESE | TOURISTS | INCREASED | | | |
| 0013 | MANY | PEOPLE | HAVE | PETS | | |
| 0014 | I | WATCH | SOCCER | ON | TV | |
| ... | | | | | | |

| ID | W1 | W2 | W3 | W4 | W5 | W6 | ... |
|---|---|---|---|---|---|---|---|
| ... | | | | | | | |
| 0031 | ONRYOU | WO | AGE | TE | KUDASAI | | |
| ... | | | | | | | |
| 0145 | ONRYOU | WO | SAGE | TE | KUDASAI | | |
| ... | | | | | | | |
| 0315 | ONDO | WO | APPU | SHI | TE | HOSHII | |
| ... | | | | | | | |
| 0423 | ONDO | WO | DAUN | SHI | TE | HOSHII | |
| ... | | | | | | | |

201D

| ID | W1 | W2 | W3 | W4 | W5 | ... |
|---|---|---|---|---|---|---|
| ... | | | | | | |
| 0031 | PLEASE | INCREASE | THE | VOLUME | | |
| ... | | | | | | |
| 0145 | PLEASE | DECREASE | THE | VOLUME | | |
| ... | | | | | | |
| 0315 | PLEASE | RAISE | THE | TEMPERATURE | | |
| ... | | | | | | |
| 0423 | PLEASE | LOWER | THE | TEMPERATURE | | |
| ... | | | | | | |

FIG. 5

| | 202A | | | | | |
|---|---|---|---|---|---|---|
| ID | W1 | W2 | W3 | W4 | W5 | W6 | ... |
| ... | | | | | | |
| 0011 | #U1# | #U1# | AGE | #U1# | #U1# | |
| 0012 | #D1# | #D1# | SAGE | #D1# | #D1# | |
| ... | | | | | | |
| 0041 | #U2# | #U2# | APPU | #U2# | #U2# | |
| 0042 | #D2# | #D2# | DAUN | #D2# | #D2# | |
| ... | | | | | | |

| | 202B | | | | |
|---|---|---|---|---|---|
| ID | W1 | W2 | W3 | W4 | W5 | ... |
| ... | | | | | |
| 0011 | #INC# | INCREASE | #INC# | #INC# | |
| 0012 | #DEC# | DECREASE | #DEC# | #DEC# | |
| ... | | | | | |
| 0041 | #UP# | UP | #UP# | #UP# | |
| 0042 | #DW# | DOWN | #DW# | #DW# | |
| ... | | | | | |

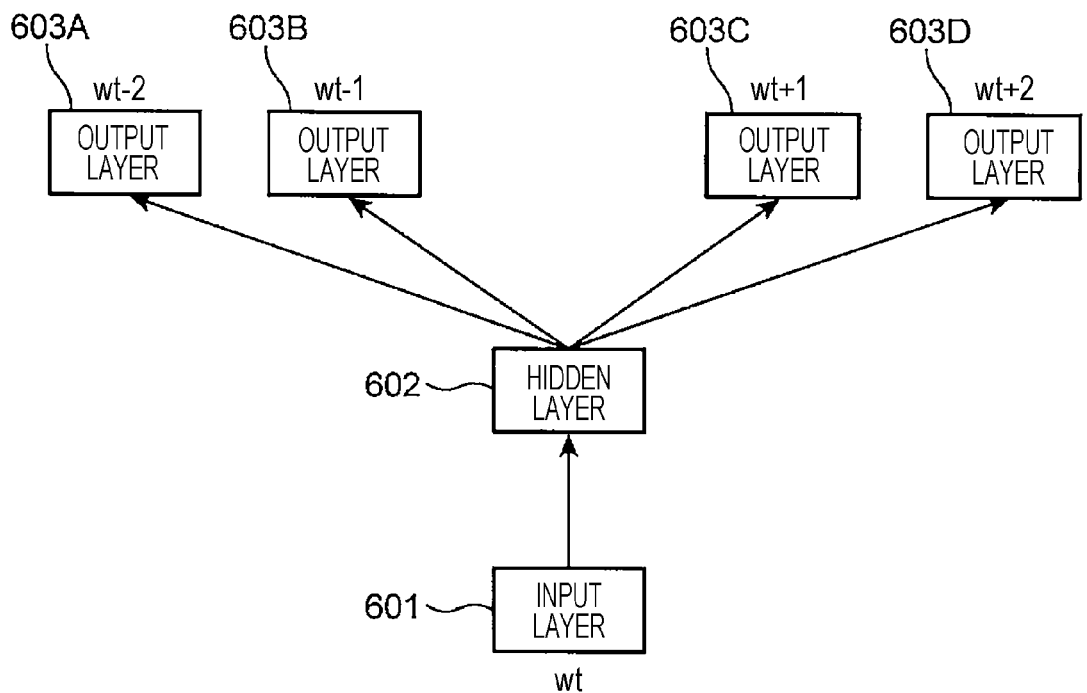

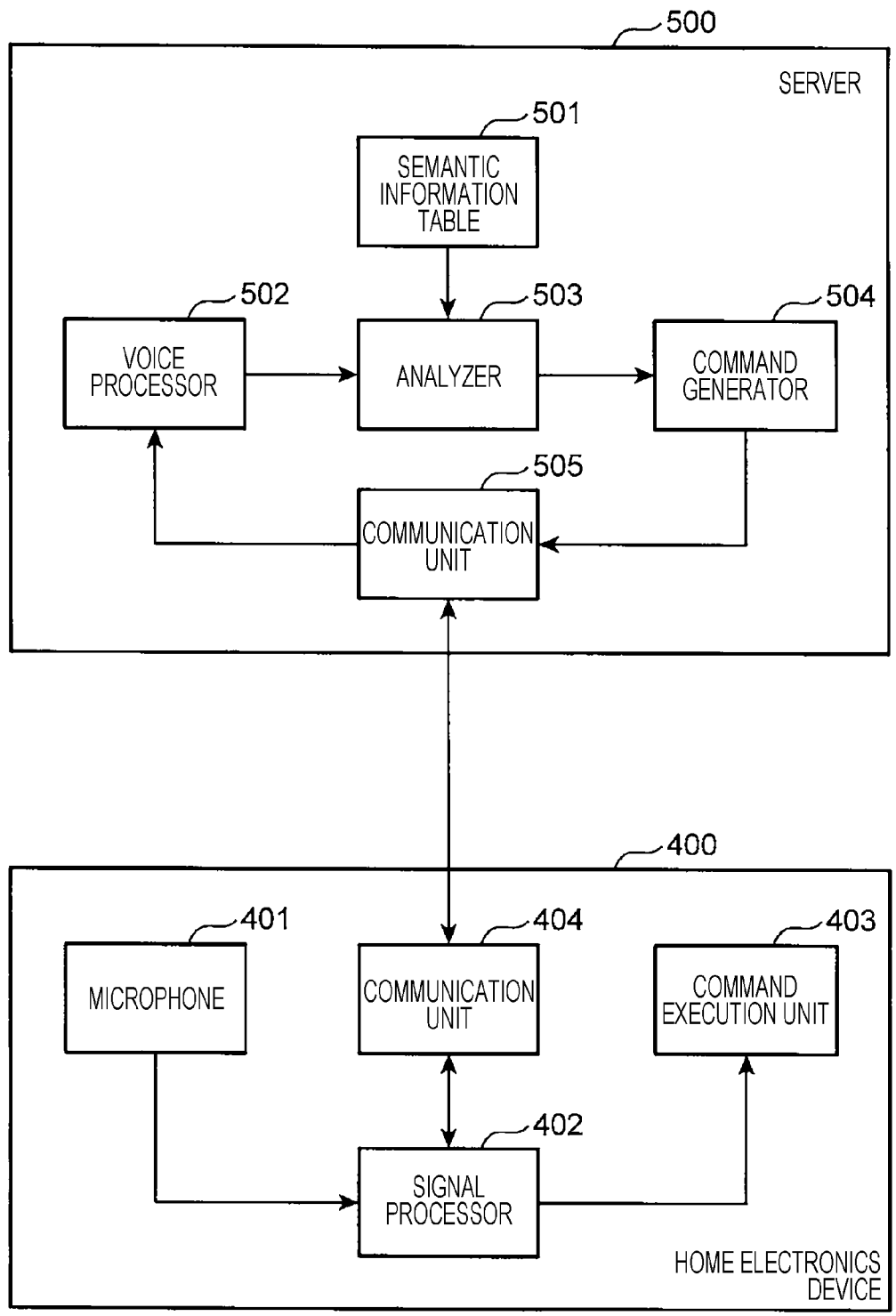

METHOD FOR ASSIGNING SEMANTIC INFORMATION TO WORD THROUGH LEARNING USING TEXT CORPUS

BACKGROUND

1. Technical Field

The present disclosure relates to an apparatus, a method, and a non-transitory computer-readable recording medium for generating semantic information concerning a word to deal with the meaning of text information in a natural language.

2. Description of the Related Art

Related art techniques generate semantic information for a word that forms text to deal with the information of text information in a natural language. The related art techniques are disclosed in Tomas Mikolov, Kai Chen, Greg Corrado, and Jeffrey Dean, "Efficient Estimation of Word Representations in Vector Space", ICLR 2013, and Tomas Mikolov, Ilya Sutskever, Kai Chen, Greg Corrado, and Jeffrey Dean, "Distributed Representations of Words and Phrases and their Compositionality", NIPS 2013. The related art techniques learn a multi-dimensional vector to be assigned to each word contained in a large amount of text data sets (hereinafter referred to as a text corpus), and then output an association between a word and a multi-dimensional vector (semantic information) corresponding to the word.

The semantic information generated in the related art techniques may be used to determine whether words are similar in meaning.

In the related art techniques, however, semantic information assigned to a given word is similar to semantic information assigned to another word which needs to be differentiated from the given word. There is still room for improvement in the determination as to whether the words are similar in meaning.

SUMMARY

In one general aspect, the techniques disclosed here feature a method for generating semantic information. The method includes acquiring a first text corpus, including first text data of a first sentence including a first word and described in a natural language, and second text data of a second sentence including a second word different in meaning from the first word, with a second word distribution indicating types and frequencies of words appearing within a predetermined range prior to and subsequent to the second word being similar to a first word distribution within the predetermined range prior to and subsequent to the first word in the first sentence, acquiring a second text corpus including third text data of a third sentence, including a third word identical to at least one of the first word and the second word, with a third word distribution within the predetermined range prior to and subsequent to the third word being not similar to the first word distribution, in accordance with an arrangement of a word string in the first text corpus and the second text corpus, performing a learning process by assigning to the first word a first vector representing a meaning of the first word in a vector space of predetermined dimensions and by assigning to the second word a second vector representing a meaning of the second word in the vector space, and storing the first vector in association with the first word, and the second vector spaced by a predetermined distance or longer from the first vector in the vector space in association with the second word.

The technique of the disclosure controls the similarity between a vector assigned to a given word and a vector assigned to another word that needs to be differentiated from the given word, and is thus used to determine whether the words are similar in meaning.

It should be noted that general or specific embodiments may be implemented as a system, a method, an integrated circuit, a computer program, a storage medium, such as a computer-readable compact disk read-only memory (CD-ROM), or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 illustrates an example of a text corpus employed as a general text corpus;

FIG. 4 illustrates an example of a text corpus employed as a general text corpus and including words in an antonym relationship;

FIG. 5 illustrates an example of text data stored on an antonym text corpus;

FIG. 6 illustrates an example of a configuration of a neural network used to calculate a probability of appearance;

FIG. 7 illustrates an example of text data used in a learning process;

FIG. 8 illustrates an example of a word represented by "1-of-K" vector;

FIG. 14 is a block diagram of a home electronics system as a second use example of the semantic information table.

DETAILED DESCRIPTION

Figure 1:
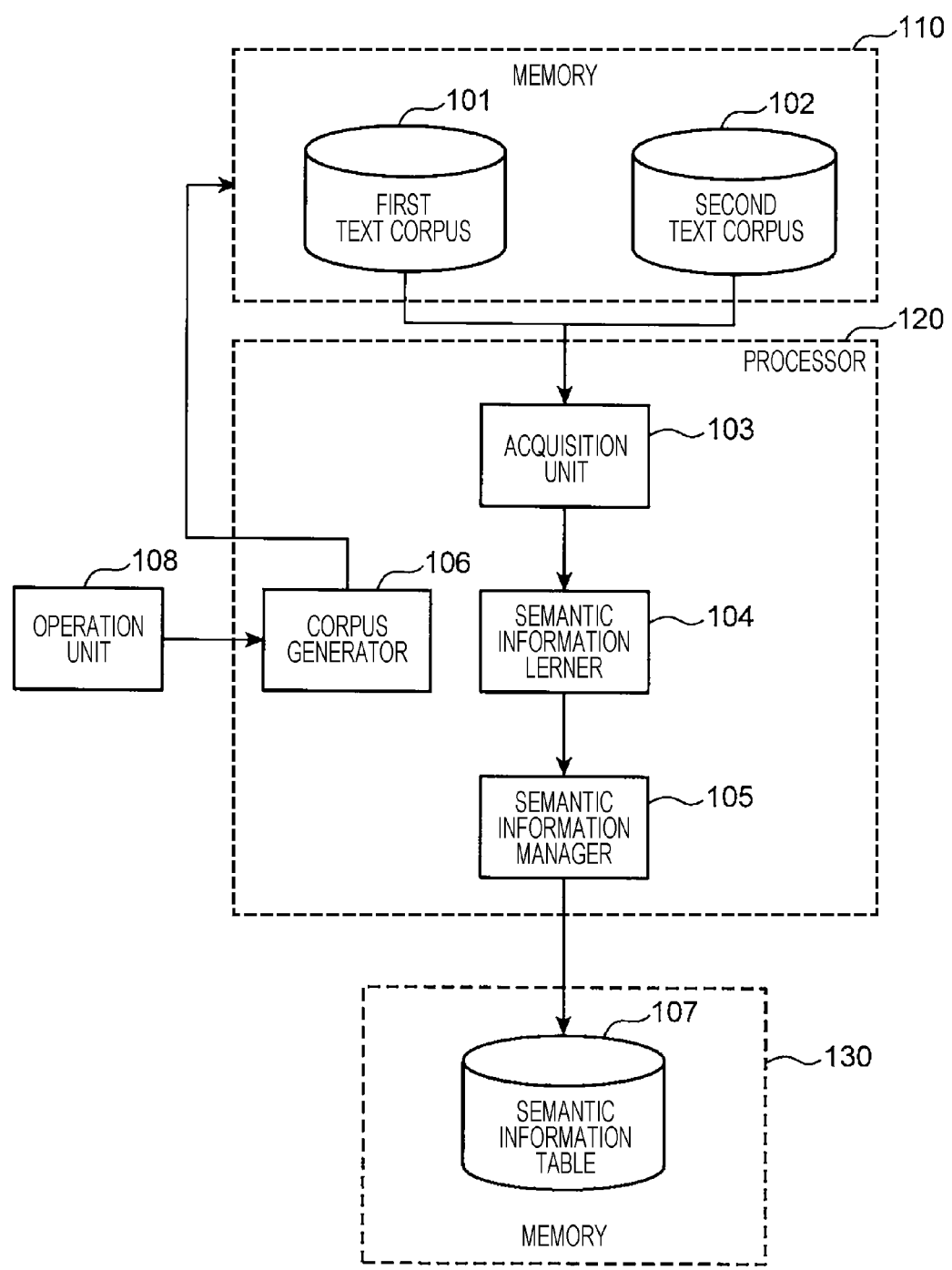
FIG. 1 is a block diagram illustrating a configuration of a word semantic information generation apparatus in accordance with an embodiment of the disclosure.

Underlying Knowledge Forming Basis of the Present Disclosure

The system of the related art for assigning a multi-dimensional vector to a word is based on the principle that is called a distributional hypothesis in the field of the natural language processing technique. The distributional hypothesis refers to the principle that words having a similar meaning are used in the same context. In other words, the distributional hypothesis refers to the principle that similar words appear prior to or subsequent to the words having a similar meaning. For example, Tomohide SHIBATA and Sadao KUROHASHI, "Context-dependent Synonymous Predicate Acquisition", Information Processing Society of Japan, Vol. 2010-NL-199 No. 13 has pointed out that words generally in an antonym relationship are similar in context, in other words, sequences of words prior to or subsequent to the words are likely to match each other or to be similar.

For example, the word "agaru (increases)" and the word "appusuru (is up)" are respectively typically used in a sentence "bonus/ga/agaru/to/ureshii" (I am happy if the bonus increases) and a sentence "bonus/ga/appusuru/to/ureshii" (I am happy if the bonus is up). In this case, the word string "bonus/ga" and the word string "to/ureshii" are common in two sentences. In the related art technique based on the distributional hypothesis, vectors having close values are assigned to words having similar contexts prior thereto and subsequent thereto in a text corpus. As a result, in the related art technique based on the distributional hypothesis, the words are converted to multi-dimensional vectors, and the words are determined to be similar in meaning depending on whether the resulting multi-dimensional vectors are similar.

However, the related art technique based on the distributional hypothesis suffers from the problem that antonyms mutually opposite in meaning have vectors having close values. For example, words "joushousuru" (rises), and "gerakusuru (falls) may appear a sentence "kabuka/wa/joushousuru/darou" (stock prices will rise) and "kabuki/wa/gerakusuru/darou" (stock prices will fall). "kabuka/ga" and "darou" commonly appear as preceding a context and a subsequent context. Based on the distributional hypothesis that words similar in meaning are used in the same context, the antonyms "joushousuru" and "gerakusuru" may be determined to have similar meaning.

Japanese Unexamined Patent Application Publication No. 2002-334077 discloses another technique that differentiates word in an antonym relationship. The disclosed technique is based on the construction of a concept base that expresses the meaning of each word with a combination of multiple attribute values. Since words in an antonym relationship in the concept base may have different attribute values, the words are thus differentiated. For example, words "an upper layer" and "a lower layer" may have an attribute value called "height". The "upper layer" has a height of a positive attribute value, and the "lower layer" has a height of a negative attribute value. The words "upper layer" and "lower layer" are thus expressed to be in an antonym relationship.

In accordance with the technique disclosed in Japanese Unexamined Patent Application Publication No. 2002-334077, an attribute value is manually described such that the words in an antonym relationship have different attribute values, or an attribute value is learned from language resource data, such as a text corpus, through an appropriate learning method. Japanese Unexamined Patent Application Publication No. 2002-334077 does not mention a specific learning method that sets different attribute values to the antonyms.

The technique disclosed in the paper "Context-dependent Synonymous Predicate Acquisition", Information Processing Society of Japan, Vol. 2010-NL-199 No. 13 has simply pointed out that words generally in an antonym relationship are similar in context, and does not specifically mention a solution to solve the problem of the related art of the distribution hypothesis.

The related art techniques are unable to assign to antonyms semantic information that appropriately clarifies a difference therebetween, through learning from the text corpus.

To solve the above problem, there is provided a method for generating semantic information. The method includes
 acquiring a first text corpus, including first text data of a first sentence including a first word and described in a natural language, and second text data of a second sentence including a second word different in meaning from the first word, with a second word distribution indicating types and frequencies of words appearing within a predetermined range prior to and subsequent to the second word being similar to a first word distribution within the predetermined range prior to and subsequent to the first word in the first sentence;
 acquiring a second text corpus including third text data of a third sentence, including a third word identical to at least one of the first word and the second word, with a third word distribution within the predetermined range prior to and subsequent to the third word being not similar to the first word distribution;
 in accordance with an arrangement of a word string in the first text corpus and the second text corpus, performing a learning process by assigning to the first word a first vector representing a meaning of the first word in a vector space of predetermined dimensions and by assigning to the second word a second vector representing a meaning of the second word in the vector space; and
 storing the first vector in association with the first word, and the second vector spaced by a predetermined distance or longer from the first vector in the vector space in association with the second word.

In this way, through the learning process from the text corpus, the method assigns, to a given word and another word that is to be differentiated from the given word, semantic information that differentiates between the two words.

More specifically, the method acquires the first text corpus that reflects the use of an actual word and the second text corpus that is produced such that word strings near a word that needs to be differentiated in meaning from the first word are not similar. Since vectors are generated as semantic information of the words from the two text corpuses, information that the word needed to be differentiated is used in a different context is reflected in the learning process of the semantic information of the word. As a result, the method is free from the problem associated with the related art techniques that the word needed to be differentiated becomes similar in meaning.

Since the semantic information expressed by the vectors of the predetermined dimensions is assigned to the first word, similarity between the first words is appropriately determined using a distance between the vectors.

The second text corpus includes the third word and a fourth word that is artificially produced and does not appear in text data of the natural language, and a word included in the predetermined range prior to and subsequent to the third word is the fourth word in the third text data.

The inclusion of the artificial word in the second text corpus reduces an adverse effect involved in the assignment of the semantic information to the word in the natural language in the text corpus. If a word near the third word is replaced with a word in the natural language, the semantic information of that word is affected by the context of the second text corpus and the semantic information different from the semantic information that is originally intended may be assigned to the word. The present embodiment is free from the above problem by replacing a word near the third word with the fourth word.

The first text data and the second text data may include a word in a first language, and in the third text data, the third word may be a word in the first language, and a word within the predetermined range prior to and subsequent to the third word is a word in a second language different from the first language.

The second word may be an antonym of the first word.

In this way, the antonyms, such as "raise" and "fall" are appropriately differentiated.

The second word may be similar in meaning to the first word, but different in terms of a degree of similarity from the first word.

In this way, the words "good", "better", and "best" that are similar in meaning may be appropriately differentiated in the degree of similarity.

The second word may be identical in concept to the first word, but different in attribute from the first word.

In this way, the words "red", "blue", and "green" belonging to the same concept "color" are thus appropriately differentiated.

The learning process may be performed using a neural network.

The semantic information is appropriately assigned to the first word and the second word in a differentiated fashion by learning the first and second text corpuses using the neural network.

The learning process may be performed using latent semantic indexing.

The semantic information is appropriately assigned to the first word and the second word in a differentiated fashion by learning the first and second text corpuses using latent semantic indexing.

The learning process may be performed using probabilistic semantic indexing.

The semantic information is appropriately assigned to the first word and the second word in a differentiated fashion by learning the first and second text corpuses using probabilistic semantic indexing.

The vector space of the predetermined dimensions may have a number of dimensions equal to a number of different types of words appearing in the first text corpus and the second text corpus.

Since this arrangement allows the semantic information to be represented by vectors having the number of dimensions equal to the number of types of words appearing in the first and second text corpuses, each word different in type is represented by a 1-of-K vector, and thus represented by a symbol string appropriate for learning.

The first text corpus may include text data in the natural language that is used to instruct a device to perform an operation, and the first word and the second word may be related to contents of the operation of the device.

Sentences "please raise the temperature", "please lower the temperature", "please turn on the air conditioner in the bedroom", and "please turn on the air conditioner in the living room" are similar but target devices are different. The difference is appropriately differentiated such that an erroneous operation to the intended device is controlled.

The first text corpus may include text data in the natural language that a patient uses i to describe a symptom of the patient in a medical diagnosis, and the first word is related to a state of the patient's body.

Descriptions of symptom, such as "my head has been hurting for these three days", and "I have been dizzy for these three days", are similar in word string, but different in meaning. These word strings are appropriately differentiated, reducing the possibility of a wrong diagnosis.

The first text corpus may include text data in the natural language that is used to describe or to treat a symptom of a patient in a medical diagnosis, and the first word may be related to a region of the patient's body.

Sentences "my right hand has been hurting for these three days", and "my stomach has been hurting for these three days", or sentences "cool your head", and "cool your right foot" are similar in word string but different in description of symptom or treatment of symptom. These word strings are appropriately differentiated, reducing the possibility of a wrong diagnosis or a wrong treatment.

The first text corpus may include text data in the natural language that is used to describe a treatment applied to a symptom of a patient in a medical diagnosis, and the first word may be related to contents of the treatment of the patient.

Description of symptoms "keep an affected area warm" and "cool an affected area" are similar in word string, but different in meaning. These word strings are appropriately differentiated, reducing a wrong instruction about the treatment.

The disclosure implements not only a word semantic information generation method configured to execute the characteristic process described above, but also a word semantic information generation apparatus including a processor configured to execute characteristic steps included in the method. The disclosure also implements a computer program causing a computer to execute the characteristic steps in the word semantic information generation method. In accordance with the disclosure, the computer program may be circulated using a non-transitory computer-readable recording medium, such as CD-ROM, or via a communication network, such as the Internet.

Embodiments of the disclosure are described below with reference to the drawings. The embodiments described below are general or specific embodiments of the disclosure. Elements, and numerical values, and shapes of the elements, steps, and the order of the steps in the embodiments are described for exemplary purposes only, and are not intended to limit the disclosure. Among the elements in the embodiments, elements not described in the independent claims indicative of higher concepts may be described as optional elements. Elements in the embodiments may be combined.

Embodiment

FIG. 1 is a block diagram illustrating a configuration of a word semantic information generation apparatus in accordance with an embodiment of the disclosure. The word semantic information generation apparatus is a computer, for example, and includes a memory 110, a processor 120, a memory 130, and an operation unit 108. Each of the memories 110 and 130 may a rewritable non-volatile memory, such as of a hard disk drive type or a solid-state drive type. The memory 110 stores a first text corpus 101 and a second text corpus 102. The memory 130 stores a semantic information table 107.

The processor 120 may be a processor, such as a central processing unit (CPU), an application-specific integrated circuit (ASIC), or a field-programmable gate array (FPGA), and includes an acquisition unit 103, a semantic information learner 104, a semantic information manager 105, and a corpus generator 106. The operation unit 108 may include an input device, such as a keyboard or a mouse, and a display device configured to display information.

Blocks in the memory 110, the processor 120, and the memory 130 are implemented when the CPU executes a computer program that causes the computer to function as the word semantic information generation apparatus.

The first text corpus 101 is an aggregate of text data in a predetermined unit including a word that serves as a generation target of the semantic information (for example, text data including a sentence as a unit). The text data is stored on the first text corpus 101 in a unit-of-word segmented state. One sentence is a word string that is ended with a punctuation mark (such as a period in English, or a small blank circle in Japanese).

The first text corpus 101 includes the aggregate of at least one piece of text data in which a word having a predetermined meaning (hereinafter referred to as a "first word") appears, and at least one piece of text data in which a word that is differentiated from the first word (hereinafter referred to as a "second word") appears.

The second text corpus 102 is an aggregate of at least one piece of text data in which a word identical to at least one of the first word and the second word (hereinafter referred to as a "third word") appears.

The text data in which the third word appears in the second text corpus 102 may be text data in a natural language, or text data including a word that is artificially produced and does not appear in a natural language (hereinafter referred to as a "fourth word"). If the fourth word is used, it is sufficient if the text data including the third word is constructed such that a distribution of a word string near the third word is set to be different from a distribution of a word string near the first word or the second word appearing in the text data included in the first text corpus 101. The "distribution of the word string near the word" is intended to mean the types of a word and the frequency of appearances of the word within a predetermined range prior to and subsequent to a target word. For example, in a sentence "onryou wo age te te kudasai" (please increase the volume), the distribution of the word string prior to and subsequent to a target word "age" is one word of onryou", one word of "wo", one word of "te", and one word of "kudadasai". The predetermined range prior to and subsequent to the target word may include the whole sentence, or a predetermined number of words including part of the whole sentence (three words, for example). The "distribution of the word string" may account for the order of appearance of the word in addition to the types of the word and the frequency of appearances of the word. The inclusion of the fourth word in the text data reduces an adverse effect that may be caused when the semantic information is assigned to a word in the natural language in the text corpus.

If a word near the third word is replaced with a word in a natural language, there is a possibility that the semantic information of that word in the natural language is affected by the context of the second text corpus 102, and that semantic information different from the semantic information that is to be originally intended to that word is assigned to that word. In accordance with the disclosure, the word near the third word is thus replaced with a fourth word.

The fourth word may be a symbol not typically used in the natural language, such as "#", "!", """, "$", or "&", or a symbol string formed of a combination thereof. If the same symbol string is frequently used as the fourth word, there is a possibility that similar semantic information is assigned to the third word. For example, a symbol or a symbol string, different from text data to text data, forming the second text corpus 102, may be used. Alternatively, a symbol or a symbol string, different from replacement target word to replacement target word, may be used. Alternatively, words having similar target words may use the same symbol or the same symbol string.

In the second text corpus 102, a word string near the third word may be text data in a natural language different from the word string near the first word. For example, text data "the room will become cool if the air conditioner is turned on" may be included in the first text corpus 101. In this case, a phrase opposite in meaning to the phrase "turned on" is "turned off", and the second text corpus 102 may include text data "the room will become hot if the air conditioner is turned off". The second text corpus 102 is thus constructed such that text data having a word of "hot" that is an antonym of "cool" is near "turned off".

If the first and second text corpuses 101 and 102 are constructed in a first predetermined language (for example, Japanese), a word string near the third word may be constructed in a second language (for example, English) different from the first language. For example, a text corpus "Eakon wo ireru to suzushii" (The room becomes cool if the air conditioner is turned on) may be included in the first text corpus 101. The second text corpus 102 may be text data "APPLE/APPLE/ireru/APPLE/APPLE" with "eakon/wo" replaced with "APPLE/APPLE", and "to/suzushii" replaced with "APPLE/APPLE".

Examples of the second word included in the first text corpus 101 and the third word included in the second text corpus 102 may include (1) an antonym of the first word included in the first text corpus 101, (2) a word similar in meaning but different in the degree of similarity from the first word included in the first text corpus 101, and (3) a word belonging to the same concept as the first word but different in attribute from the first word in the first text corpus 101.

In the case of antonyms, "ageru" (raise) and "sageru" (lower) may be differentiated. If the words are similar but different in the degree of similarity, "good", "better", and "best", which are similar but different in the degree of similarity, may be differentiated. Words may belong to the same concept but different in attribute. For example, "red", "blue", and "green" that fall within the same concept of "color" may be differentiated as words different in attribute.

The acquisition unit 103 acquires the first text corpus 101 and the second text corpus 102. If the memory 110 is a local storage device, the acquisition unit 103 may simply read the first and second text corpuses 101 and 102 from the memory 110. If the memory 110 is an external storage device connected via a communication network, the acquisition unit 103 accesses the memory 110 via the communication network, and then acquires the first and second text corpuses 101 and 102.

The semantic information learner 104 treats as a target word a word appearing in the text data contained in the first text corpus 101 and the second text corpus 102. The semantic information learner 104 performs a learning process to assign semantic information to the target word such that the target word is similar in meaning to a word that is similar to the target word in terms of a distribution of a word string appearing within a predetermined range prior to and subsequent to the target word.

The semantic information to be assigned to the target word may be expressed so that a semantic vector having a predetermined dimension number differentiates the semantic information. In this way, the degree of similarity between the words is appropriately determined using a distance between the semantic vectors.

The semantic vector has a number of dimensions equal to the number of types of words appearing in the first and second text corpuses 101 and 102. The words different in type may be expressed in 1-of-K vector, and thus expressed by a symbol string appropriate for learning.

The semantic information may be expressed by coordinates information of a point corresponding to an end point of a vector rather than by a vector in a vector space of predetermined dimensions.

The semantic information may be expressed in a predetermined format that allows to be calculated the degree of similarity indicating how much the words are similar in meaning. The predetermined format that allows the degree of similarity to be calculated may be the semantic vector, or a distance from a reference point (such as the origin) to the front end of each semantic vector in the vector space. If the distance is used, words placed at the same distance from the reference point are not differentiated from each other, but words placed at different distances from the reference point are differentiated from each other. Since the degree of similarity is represented by a scalar quantity in such a case, a workload to calculate the degree of similarity between the words is reduced.

The semantic information learner 104 may use a neural network, latent semantic indexing or probabilistic semantic indexing in the learning process.

The semantic information manager 105 manages the semantic information table 107 that indicates the assignment state of the semantic information to the target word as a result of learning by the semantic information learner 104. The "target word" indicates a word that serves as a target to which the semantic information is assigned, and includes the first word and the third word. The fourth word may or may not be the target word.

The semantic information table 107 stores, in a table format, an association between each word and the semantic information assigned to the word.

The corpus generator 106 generates the second text corpus 102 using the first text corpus 101. The second text corpus 102 may be artificially or automatically generated. If the second text corpus 102 is artificially generated, the corpus generator 106 may generate the second text corpus 102 in response to an operation that is performed by an operator using the operation unit 108. The operator may enter an operation to edit the first text corpus 101 one sentence by one sentence, thereby causing the corpus generator 106 to generate the second text corpus 102.

When the second text corpus 102 is automatically generated, the corpus generator 106 extracts from the text data forming the first text corpus 101 a pair of words having meanings in a predetermined relationship as the first and third words. The corpus generator 106 replaces a word string appearing within a predetermined range prior to and subsequent to the extracted first word with a predetermined word, and replaces a word string appearing within a predetermined range prior to and subsequent to the extracted third word with a predetermined word. The corpus generator 106 then stores the resulting text data on the second text corpus 102. The predetermined word may be the fourth word or the second word. Using predetermined different words, the corpus generator 106 performs the replacement operation on the text data including the first word, and the text data including the third word paired with the first word. When the first word and the third word, having meanings in a predetermined relationship, are extracted, the corpus generator 106 may use an association table in which an association relationship between the words is registered in advance. If an antonym is used as the third word, the association table may register the association relationship, such as "hot"-"cool", in advance. The corpus generator 106 may not necessarily have to perform the word replacement on the text data including the first word.

In an example described below, a word included in the second text corpus 102 is an antonym of a word included in the first text corpus 101.

Figure 2:
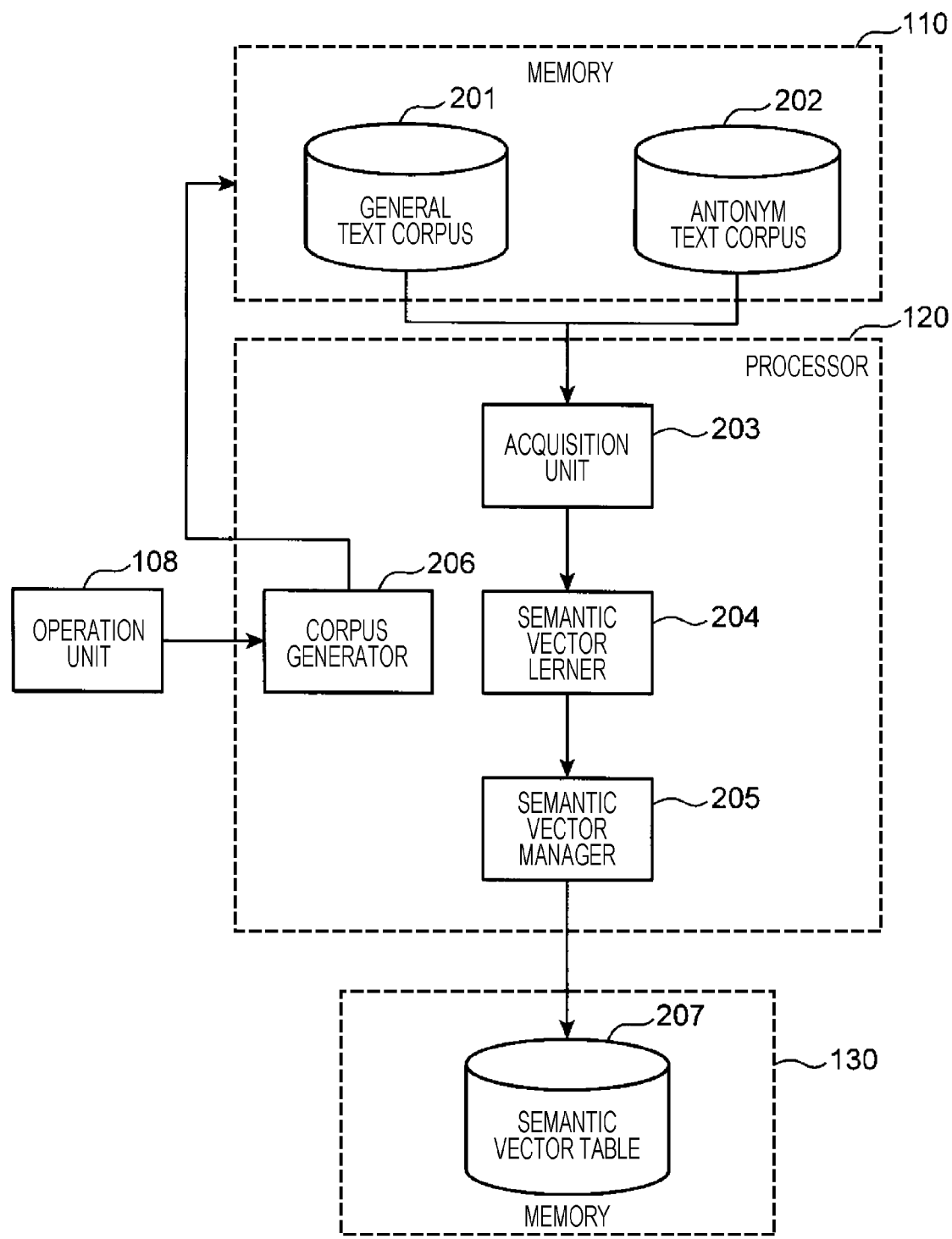
FIG. 2 is a block diagram illustrating an example of a configuration of the word semantic information generation apparatus when a word included in a second text corpus is an antonym of a word included in a first text corpus.

FIG. 2 is a block diagram illustrating an example of a configuration of the word semantic information generation apparatus when a word included in the second text corpus 102 is an antonym of a word included in the first text corpus 101. Referring to FIG. 2, elements identical to those of FIG. 1 are designated with the same reference numerals and the discussion thereof is omitted.

As illustrated in FIG. 2, a general text corpus 201 is an aggregate of multiple pieces of text data in predetermined units including a word that is a target of the semantic information (for example, text data including a sentence handled as a unit).

FIG. 3 illustrates an example of text corpuses 201A and 201B employed as the general text corpus 201. Referring to FIG. 3, the text corpus 201A is an example of a Japanese general text corpus 201. Japanese is typically described in a character string of words with no delimitation. Morphological analysis software (such as MeCab) may derive word string data delimited by word unit from character string data with no word delimitation. In the example of FIG. 3, a unit of the text data included in the text corpus 201A is a unit of sentence. Multiple pieces of text data in the text corpus 201A are respectively identified by identification numbers (ID as illustrated in FIG. 3). The text corpus 201A also stores words in the order of appearance forming each piece of text data. Each word in the text data is identified by index information (W1 through W6 of FIG. 3).

Referring to FIG. 3, the text corpus 201B is an example of an English general text corpus 201. English is typically a character string that is delimited by a space, and the character string is segmented by each space to obtain word string data. As in the text corpus 201A, the unit of text data is a unit of sentence in the text corpus 201B, and the text data is identified by identification information (ID of FIG. 3). As in the text corpus 201A, each word in the text data is identified by index information (W1 through W5 of FIG. 3) in the text corpus 201B.

FIG. 4 illustrates text corpuses 201C and 201D used as a general text corpus 201. The text corpuses 201C and 201D include words in an antonym relationship. The text corpus 201C is a Japanese text corpus, and includes text data where "age" (raise) appears, and text data where "sage" (lower) appears. The text corpus 201C includes another text corpus, and includes text data where "appu" (up) appears, and text data where "daun" (down) appears.

Word strings appearing prior to and subsequent to words "age" and "sage" are "onryou/wo" and "te/kudasai" and are common to the words. Word strings appearing prior to and subsequent to words "appu" and "daun" are "ondo/wo" and "shi/te/hoshii" and are common to the words. As described in the paper "Context-dependent Synonymous Predicate Acquisition", Information Processing Society of Japan, Vol. 2010-NL-199 No. 13, an antonym has typically a similar context where an antonym appears. More specifically, word strings prior to and subsequent to an antonym match or are similar to each other.

The text corpus 201D is an example of an English text corpus, and includes text data where "increase" appears, and text data where "decrease" appears. The text corpus 201D also includes text data where "raise" appears, and text data where "lower" that is an antonym of "raise" appears. In this example, word strings prior to and subsequent to "increase" and "decrease" are "please" "the/volume" and are thus common to the words. Word strings prior to and subsequent to "raise" and "lower" are "please" "the/temperature" and are thus common to the words.

The phenomenon that the contexts including a word and an antonym of the word look similar is commonly recognized not only both in Japanese and English but also in other languages.

The antonym text corpus 202 of FIG. 2 is an aggregate of text data in predetermined units (for example, text data in units of sentences) including at least one of words in an antonym relationship in the general text corpus 201. As the general text corpus 201, the text data in the antonym text corpus 202 is segmented by the word unit and then stored.

FIG. 5 illustrates an example of text data stored in the antonym text corpus 202. Referring to FIG. 5, a text corpus 202A is an example of a Japanese antonym text corpus 202. The text corpus 202A includes text data where "age" appears, and text data where "sage" appears. In the text data where "age" appears, word strings appearing prior to and subsequent to "age" are "#U1#/#U1#", and "#U1#/#U1#". In other words, as illustrated in FIG. 4, the text data reading "onryou/wo/age/te/kudasai" is replaced with "#U1#/#U1#/age/#U1#/#U1#".

On the other hand, word strings appearing prior to and subsequent to "sage" are "#D1#/#D1#", and "#D1#/#D1#". In other words, as illustrated in FIG. 4, the text data reading "onryou/wo/sage/te/kudasai" is replaced with "#D1#/#D1#/age/#D1#/#D1#".

The words (symbols) "#U1#" and "#D1#" are examples of the fourth word, and is an artificially generated words that do not appear in natural languages. More specifically, the words (symbols) "#U1#" and "#D1#" do not appear in the text data of the general text corpus 201.

The text corpus 202A is generated using the fourth words "#U1#" and "#D1#" such that the word strings prior to and subsequent to "age" and "sage" are different. The same is true of "appu" and "daun" in an antonym relationship. The text corpus 202A is generated using the fourth words "#U2#" and "#D2#" such that word strings prior to and subsequent to "appu" and "daun" are different. If the learning process is performed using the text corpuses 201A and 202A, the semantic information may be assigned such that the antonyms are clearly differentiated.

Referring to FIG. 5, the text corpus 202B is an example of an English version of the antonym text corpus 202. The text corpus 202B includes text data where "increase" appears, and text data where "decrease" that is an antonym of "increase" appears. In these two pieces of text data, word strings appearing prior to and subsequent to "increase" are "#INC#" and "#INC#/#INC#. Referring to FIG. 4, the text data reading "please/increase/the/volume" is replaced with "#INC#/increase/#INC#/#INC#.

On the other hand, the word strings appearing prior to and subsequent to "decrease" are "#DEC# and "#DEC#/#DEC#". Referring to FIG. 4, the text data reading "please/decrease/the/volume" is replaced with "#DEC#/decrease/#DEC#/#DEC#.

As in the text corpus 202A, the words (symbols) "#INC#" and "#DEC#" are examples of the fourth word, and are artificially generated words that do not appear in a typical natural language.

The text corpus 202B is generated using the fourth words "#INC#" and "#DEC#" such that the word strings prior to and subsequent to "increase" and "decrease" in an antonym relationship are different. Concerning "raise" and "lower" in an antonym relationship, the text corpus 202B is generated using fourth words "#UP#" and "#DW#" such that words appearing prior to and subsequent to "raise" and "lower" become different. Learning the text corpuses 201B and 202B causes the semantic information to be assigned such that a word and the antonym of the word are clearly differentiated.

Referring to FIG. 5, one or two words immediately prior to or immediately subsequent to the target word are replaced with the fourth word. The disclosure is not limited to this arrangement. Three or more words immediately prior to or immediately subsequent to the target word are replaced with the fourth word. The disclosure is not limited to this arrangement. The number of words, to be replaced with the fourth word, immediately prior to or immediately subsequent to the target word may not necessarily have to be equal to the number of words immediately prior to or immediately subsequent to the target word in the general text corpus 201. In the text corpus 202B, one word immediately prior to "increase" or "decrease" is replaced. Alternatively, the word may be replaced with two or more fourth words or one or less fourth word.

A word immediately prior to or immediately subsequent to "increase" or "decrease" is replaced in the text corpus 202B, because there is one word immediately prior to or immediately subsequent to "increase" or "decrease" in the original text data. If there are two or more words immediately prior to or immediately subsequent to "increase" or "decrease", the two or more words are replaced with the fourth word.

As illustrated in FIG. 5, the same fourth word is used in a single piece of text data. This is described for exemplary purposes only, and a different fourth word may be used for a different target word to be replaced.

As illustrated in FIG. 2, an acquisition unit 203 acquires the general text corpus 201 and the antonym text corpus 202.

With reference to FIG. 2, a semantic vector learner 204 (part of a semantic information learner) uses the text data included in the general text corpus 201 and the text data included in the antonym text corpus 202. The semantic vector learner 204 performs the learning process to assign a semantic vector (an example of the semantic information) to a target word appearing in the text corpus such that the target word is similar in meaning to a word that is similar to the target word in terms of a distribution of a word string appearing within a predetermined range prior to and subsequent to the target word. The semantic vector is numerical information of at least one dimension that represents the meaning of a word.

A semantic vector manager 205 (an example of a semantic information manager) manages a semantic vector table 207 (an example of the semantic information) that is a learning result of the semantic vector learner 204 and indicates an assignment state of the semantic information to the target word.

As the corpus generator 106, a corpus generator 206 generates the antonym text corpus 202 from the general text corpus 201.

The semantic vector table 207 stores in a table an association relationship between each word and a semantic vector responsive to the word.

The assignment of a semantic vector to a word is based on the principle that semantic vectors having close values are assigned to words having similar contexts, namely, words having similar word strings appearing prior thereto or subsequent thereto. Learning systems that learn the semantic vector, based on the principle, are implemented using the techniques disclosed in Tomas Mikolov, Kai Chen, Greg Corrado, and Jeffrey Dean, "Efficient Estimation of Word Representations in Vector Space", ICLR 2013, and Tomas Mikolov, Ilya Sutskever, Kai Chen, Greg Corrado, and Jeffrey Dean, "Distributed Representations of Words and Phrases and their Compositionality", NIPS 2013.

In accordance with the present embodiment, semantic information is assigned to a word using the technique disclosed in the paper "Distributed Representations of Words and Phrases and their Compositionality". The technique disclosed in the paper "Distributed Representations of Words and Phrases and their Compositionality" is briefly described. As in formula (1), the semantic vector learner 204 expresses the text data with a word string W including the number of words T (T is an integer equal to 1 or above). More specifically, the semantic vector learner 204 extracts all words appearing in all the text data included in the general text corpus 201 and the antonym text corpus 202, and replaces each word with a 1-of-K vector, and then organizes the text data as the word string W as a 1-of-K string.

$$W = w_1, w_2, w_3, \ldots, w_T \quad (1)$$

$$\frac{1}{T}\sum_{t=1}^{T} \sum_{-c \leq j \leq c, j \neq 0} \log p(w_{t+j} | w_t) \quad (2)$$

The objective of the learning process is maximizing a value defined by formula (2).

Formula (2) means that a logarithm sum of a conditional appearance probability of c words wt+j (c is an integer equal to or above 1) appearing prior to and subsequent to a word wt placed at a t-th position of a word string W is averaged with respect to each of all words of the word string W. Here, j represents an index that identifies c words appearing prior to and subsequent to the word wt, and is represented by an integer within a range of −c through c except zero. Maximizing formula (2) means that the word wt+j output in response to the inputting of the word wt becomes at a higher probability a word that appears prior to and subsequent to the word wt in learning data.

In the paper "Distributed Representations of Words and Phrases and their Compositionality", the computation of the conditional appearance probability of formula (2) is modeled in a three-layer neural network. FIG. 6 illustrates an example of the configuration of the neural network used to calculate a probability of appearance.

The neural network of FIG. 6 is an example in which c=2 in formula (2). More specifically, a link state of the layers forming the neural network is learned such that the conditional appearance probability related to a total of four words wt−2, wt−1, wt+1, and wt+2, namely, two words prior to the word wt and two words subsequent to the word wt is maximized.

Referring to FIG. 6, an input layer 601 receives the word wt. For example, in text data "kyou/no/tenki/wa/yoku/naru/yohou/ga/dete/iru" (the weather forecast says it's fine today) as illustrated in FIG. 7, let the word "yoku" in the words to be the word wt, and a vector corresponding to the word "yoku" is input to the input layer 601.

The vector corresponding to the word wt is expressed in a 1-of-K format. If the number of types of words appearing in the text corpus of learning data is K, the dimension of a t-th vector of K dimensions corresponding to t-th word with K words lined up (t is an integer equal to or below K) is "1", and the other elements have "zero". This is called 1-of-K format.

The text corpus of a large size is typically the learning data. The number of types of words ranges from tens of thousands to hundreds of thousands, and the word wt is represented by a vector of tens of thousands to hundreds of thousands of dimensions. For example, the number of types of words is about 200,000 in Japanese newspaper articles. If the newspaper articles are the learning data, the word wt is represented by a vector of about 200,000 dimensions. If the word wt is represented by a vector of K dimensions, the input layer 601 includes K nodes.

FIG. 8 illustrates an example of the word wt represented by a 1-of-K vector. Referring to FIG. 8, the words "tenki", "wa", "yoku", "naru", and "yohou" are represented by 1-of-K vectors. For example, let the word "tenki" be a word lined up at the t-th position from among the K words serving as the learning data. The t-th dimension only is "1", and "0" is assigned to the other dimensions. Since "wa" follows "tenki", (t+1)-th element is "1", and "0" is assigned to the other elements. The other words are also represented by 1-of-K vectors. Since a vector is assigned to each word such that the location of appearance of "1" is different. The semantic vector learner 204 thus differentiates the words in accordance with the location where "1" appears. The arrangement of the K words is not limited to any particular method. The K words may be in the order of appearance in the text corpus or in a random order.

Referring to FIG. 6, the elements of the vectors input to the input layer 601 are combined in a weighted linear manner, and the resulting scalar quantity is converted into a layer of vectors using an activation function. The layer of vectors is the hidden layer 602.

The number of dimensions of the vector in the hidden layer 602 may be set to any value. The number of dimensions typically set is smaller than the number of dimensions (K dimensions) of the vector at the input layer 601. In the technique disclosed in the paper "Distributed Representations of Words and Phrases and their Compositionality", the number of dimensions of the vector at the hidden layer 602 is 200 dimensions as a default value.

Referring to FIG. 6, the output layers 603A, 603B, 603C, and 603D are vector layers that are obtained by combining the elements of the vectors at the hidden layer 602 in the weighted linear manner, and converting the resulting scalar values using a Softmax function. The output layers 603A, 603B, 603C, and 603D respectively represent appearance probability distributions of the words wt−2, wt−1, wt+1, and wt+2. If the number of types of words included in the text corpus is K, the vectors of the output layers 603A, 603B, 603C, and 603D have respectively K dimensions. The value of a k-th element indicates the appearance probability of the k-th word wk.

X represents a vector at the input layer 601, H represents a vector at the hidden layer 602, and Y(−2), Y(−1), Y(+1), and Y(+2) respectively represent vectors at the output layers 603A, 603B, 603C, and 603D. Formula (3) derives the vector H from the vector X, and formula (4) derives an i-th element of the vectors Y(−2), Y(−1), Y(+1), and Y(+2) from the vector H.

$$H = W^{XH} \cdot X \qquad (3)$$

$$Y_{i(j)} = \frac{\exp(I_i^T \cdot W_{(j)}^{HY} \cdot H)}{\sum_k \exp(I_k^T \cdot W_{(j)}^{HY} \cdot H)} \qquad (4)$$

WXH in formula (3) is a matrix that represents weights used when the elements of the vector X are combined in the weighted linear manner. Vectors Ii and Ik in formula (4) are K dimensional vectors respectively with an i-th element and a k-th element at "1", and other elements having "0".

Weighting matrix W(j) HY of formula (4) represents weights used when the vector H is combined in a weighted linear manner. The numerator of formula (4) represents an exponential function value with an argument that results from linear combining the vector H with i-th row vector of the weighting matrix W(j) HY. The denominator of formula (4) is the sum of exponential function values with arguments that result from linear combining the vector H with the first row to K-th row vectors of the weighting matrix W(j) HY.

Figure 9:
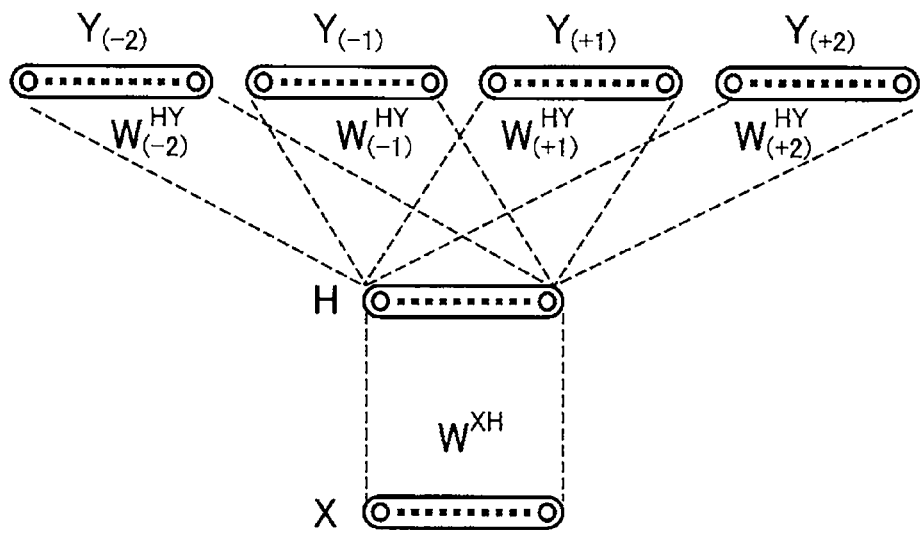
FIG. 9 illustrates the neural network of FIG. 6 using vectors X, H, Y(−2), Y(−1), Y(+1), and Y(+2)

FIG. 9 illustrates the neural network of FIG. 6 using the vectors X, H, Y(−2), Y(−1), Y(+1), and Y(+2). Using the neural network thus organized, the semantic vector learner 204 determines the values of a matrix representing weights through backpropagation learning, with the word wt appearing in the text data in the text corpus as an input teacher signal and the word wt+j (−c≤j≤c, and j≠0) as an output teacher signal.

If the semantic vector learner 204 is constructed in accordance with the method disclosed in the paper "Distributed Representations of Words and Phrases and their Compositionality", the weighting matrix WXH is used as the semantic vector table 207. If each word is expressed in a 1-of-K vector, the weighting matrix WXH is represented by a matrix of S rows and K columns. S is the number of dimensions of the vector at the hidden layer 602.

A j-th column of the weighting matrix WXH is a 1-of-K vector, and is a semantic vector with a j-th element being 1. The semantic vector table 207 may include in addition to the weighting matrix WXH a table indicating an association relationship of a word that is assigned to each column of the weighting matrix WXH.

The weight matrices W(−2)HY, W(−1) HY, W(+1)HY, and W(+1)HY are needed in a learning phase that is based on the backpropagation learning, but becomes unnecessary when the learning phase is complete. In a use phase with the semantic vector table 207 used, only the weighting matrix WXH is used.

Figure 10:
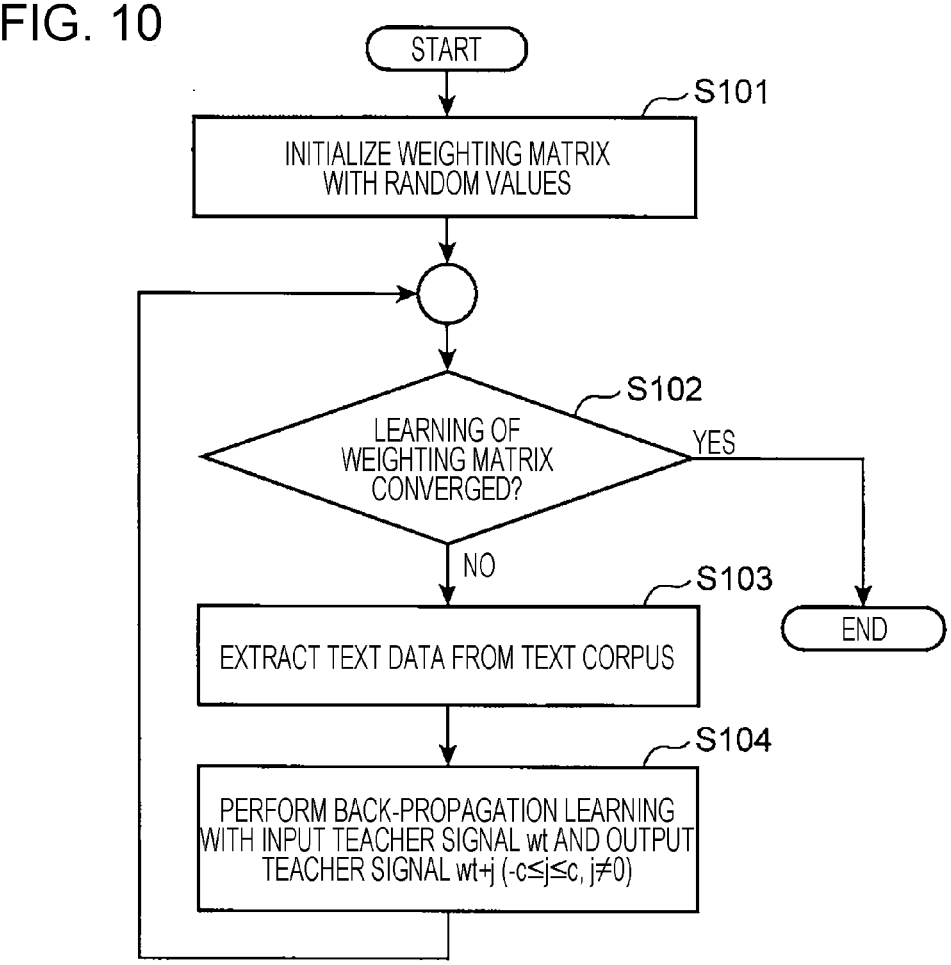
FIG. 10 is a flowchart illustrating a learning process of the word semantic information generation apparatus of an embodiment of the disclosure.

FIG. 10 is a flowchart illustrating a learning process of the word semantic information generation apparatus of the embodiment of the disclosure.

The semantic vector learner 204 initializes the weighting matrices WXH and WHY of the neural network with random values (step S101). The semantic vector learner 204 determines whether the learning process has converged with a change in the weighting matrices WXH and WHY through the backpropagation learning equal to or below a predetermined value (step S102). If the learning process has converged (yes branch from step S102), the semantic vector learner 204 ends the learning process. If the weighting matrices WXH and WHY are not below the predetermined values, the semantic vector learner 204 determines that the learning process has not converged (no branch from step S102), and then proceeds to step S103.

The acquisition unit 203 acquires a piece of text data from the text corpuses as a learning target (step S103). The text corpuses as a learning target are the general text corpus 201 and the antonym text corpus 202. The acquisition unit 203 may simply extract a piece of text data from the two text corpuses.

The semantic vector learner 204 varies the values of the weighting matrices WXH and WHY through the backpropagation learning with the word wt appearing in the extracted text data as an input teacher signal and the word wt+j (−c≤j≤c, and j≠0) as an output teacher signal (step S104), and then returns to step S102.

The semantic vector learner 204 is extracting the text data one piece by one piece from the text corpus as the learning target until the change in the value the weighting matrices WXH and WHY becomes lower than the threshold value. Even if all the text data is extracted from the text corpus as the learning target, the learning process may not converge. In such a case, the acquisition unit 203 extracts the text data, starting with first text data again. In other words, the text data is cyclically extracted from the text corpus as the learning target in the learning process to converge the values of the weighting matrices WXH and WHY.

As described above, the semantic vector learner 204 receives a given word with the text data in the text corpus as a teacher signal, modifies the weighting matrix of the neural network such that the appearance probability of words prior to and subsequent to that input word becomes higher, thereby learning the semantic vector to be assigned to that word. From among multiple words included in the text corpus, words having word strings appearing prior thereto or subsequent thereto and being mutually similar to each other in meaning may be naturally similar in semantic vector that are learned. This is because the learning process is performed based on the distribution hypothesis that words similar to each other in meaning appear in similar contexts.

However, in a real natural language, antonyms also appear with similar contexts. As described with reference to the general text corpuses 201C and 201D of FIG. 4, the contexts of the words in an antonym relationship have frequently identical or similar word strings prior thereto or subsequent thereto. If the learning process based on the distribution hypothesis is performed on a text corpus collected in an ordinary manner and serving as the learning data, the semantic vectors assigned to the words in an antonym relationship are similar, and it is difficult to clearly differentiate one word from another.

Figure 11:
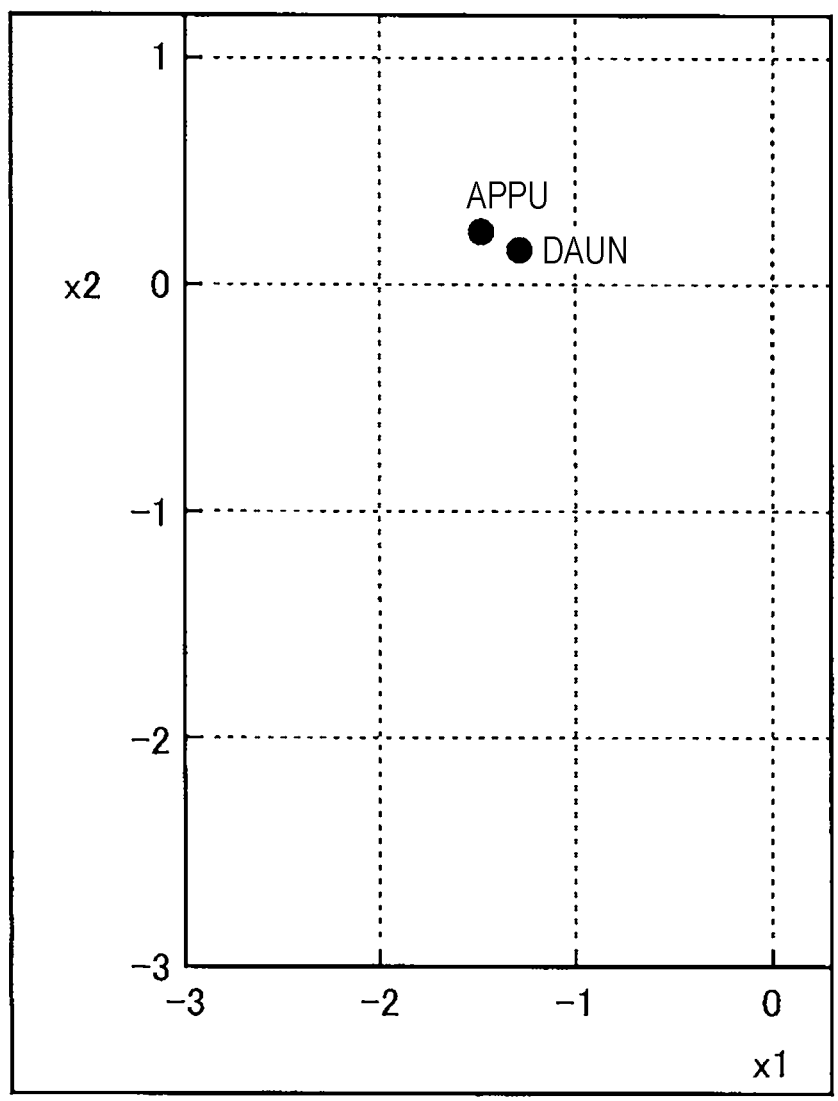
FIG. 11 is a graph in which semantic vectors assigned to the word "appu" and the word "daun" are reduced to two dimensions through a principal component analysis in a semantic vector table of a comparative example to the embodiment.

FIG. 11 is a graph in which semantic vectors assigned to the word "appu" and the word "daun" are reduced to two dimensions through a principal component analysis in a semantic vector table of a comparative example to the embodiment. The semantic vector table of the comparative example is obtained by performing the distribution hypothesis based learning process on a text corpus that has been produced by performing morphological analysis in the Japanese version Wikipedia. As illustrated in FIG. 11, the word "appu" and the word "daun" are closely located and very close semantic vectors are assigned to the two words.

Figure 12:
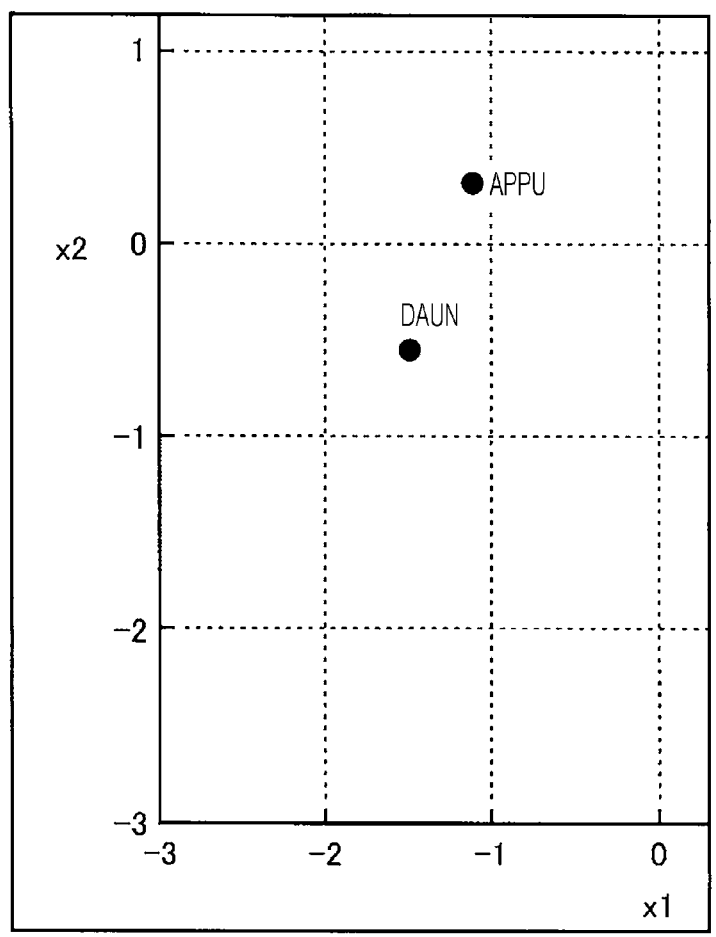
FIG. 12 is a graph in which semantic vectors assigned to the word "appu" and the word "daun" are reduced to two dimensions through the principal component analysis in the semantic vector table of the embodiment.

FIG. 12 is a graph in which semantic vectors assigned to the word "appu" and the word "daun" are reduced to two dimensions through the principal component analysis in the semantic vector table 207 of the embodiment. Referring to FIG. 12, the text corpus produced from the Japanese version of Wikipedia is used as the general text corpus 201. Used as the antonym text corpus 202 is the text corpus that is produced for antonyms including the word "appu" and the word "daun" such that the contexts of the antonyms 202A of FIG. 5 are different. The distribution hypothesis learning is performed on the two text corpuses to produce the semantic vector table 207.

More specifically, the semantic vector table 207 stores a first word and a first vector representing the meaning of the first word in association with each other and a second word and a second vector in association with each other with the second vector spaced apart by a predetermined distance or longer from the first vector in a vector space.

As illustrated in FIG. 12, the word "appu" and the word "daun" are spaced much more than those words in FIG. 11. This means that substantially different semantic vectors are assigned to those words.

The word semantic information generation apparatus of the embodiment uses the antonym text corpus 202 in addition to the general text corpus 201. The antonym text corpus 202 is generated in a manner such that the contexts of the words in an antonym relationship are different. Since the distribution hypothesis learning process is performed on the two corpuses, the semantic vector is assigned to each word such that the words in an antonym relationship are appropriately differentiated.

The disclosure has been discussed with reference to the case in which a given word and an antonym of the given word are differentiated. The disclosure may find applications in the following specific examples.

(1) The first text corpus 101 includes the text data in a natural language used to instruct a device to operate, and the second text corpus 102 is constructed such that a word related to operation contents of the device is included as the third word. For example, sentences "please raise the temperature", "please lower the temperature", "please turn on the air-condition in the bedroom", and "please turn on the air-conditioner in the living room" are similar in word string but different in meaning from each other. The instructions intended by these sentences are thus appropriately differentiated, thereby controlling an erratic operation of the devices.

(2) The first text corpus 101 may include text data in a natural language that a patient uses to describe his or her symptom in a medical diagnosis. The second text corpus 102 is constructed such that a word related to a state of the patient's body is included as the third word. In this way, sentences "my head has been hurting for these three days", and "I have been dizzy for these three days" are similar in word string but quite different in meaning. The descriptions of the symptoms are appropriately differentiated, leading to controlling a wrong diagnosis.

(3) The first text corpus 101 may include text data in a natural language that is used to explain a symptom of a patient in a medical diagnosis or to treat the symptom. The second text corpus 102 is constructed such that a word related to a region of the patient's body is included as the third word. In this way, sentences "my right hand has been hurting for these three days", and "my stomach has been hurting for these three days", or sentences "cool your head", and "cool your right foot" are similar in word string but different in description of symptom or treatment of symptom. These word strings are appropriately differentiated, reducing the possibility of a wrong diagnosis or a wrong treatment.

(4) The first text corpus 101 may include text data in a natural language that is used to explain a treatment to a symptom of a patient in a medical diagnosis. The second text corpus 102 is constructed such that a word related to contents of the treatment is included as the third word. In this way, sentences "keep an affected area warm" and "cool an affected area" are similar in word string, but different in meaning. These word strings are appropriately differentiated, reducing a wrong instruction about the treatment.

Figure 13:
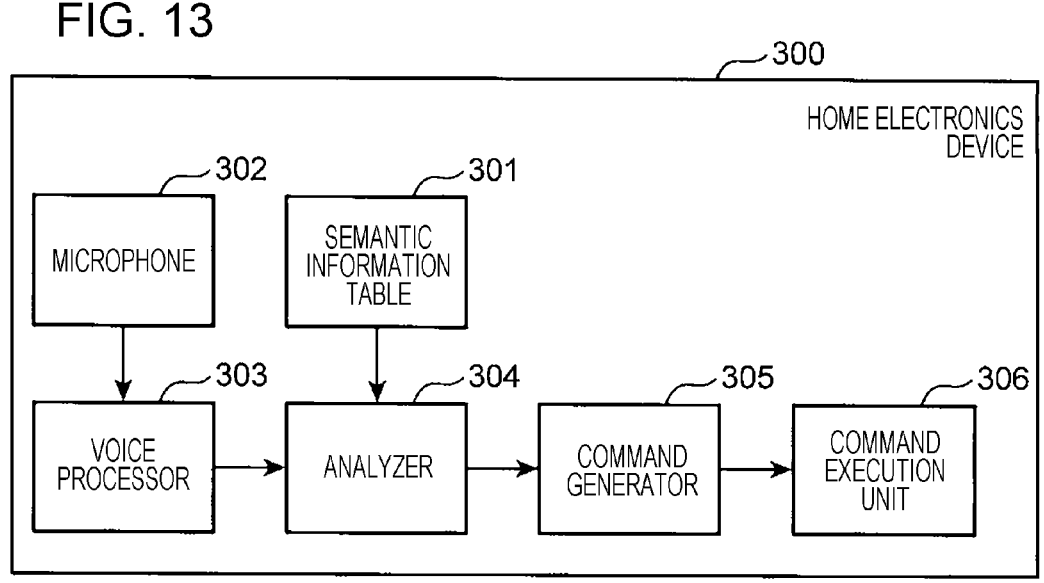
FIG. 13 is a block diagram of a home electronics device as a first use example of a semantic information table.

The use of a semantic information table produced through the learning process is described below. FIG. 13 is a block diagram of a home electronics device 300 as a first use example of the semantic information table.

The home electronics devices 300 include a variety of home electronics including a television, an audio device, a washing machine, an air-conditioner, a refrigerator, and a light.

The home electronics device 300 includes a semantic information table 301, a microphone 302, a voice processor 303, an analyzer 304, a command generator 305, and a command execution unit 306. The semantic information table 301 is a table that is obtained by learning the first and second text corpuses 101 and 102 illustrated in FIG. 1, and corresponds to the semantic information table 107 of FIG. 1.

The microphone 302 converts a voice of a user into an electrical audio signal and is used to pick up the voice of the user. The voice processor 303 analyzes the audio signal output from the microphone 302, and generates text data indicating the voice spoken by the user. The analyzer 304 analyzes the text data generated by the voice processor 303 using the semantic information table 301. The analyzer 304 determines the semantic information of each word forming the input text data by referencing the semantic information table 301. The analyzer 304 references the determined semantic information of each word to determine whether the contents of the voice of the user are related to an operation of the home electronics device 300. If the contents of the voice of the user are related to an operation of the home electronics device 300, the analyzer 304 outputs operation information related to the operation to the command generator 305.

The command generator 305 generates a command to perform an operation indicated by the input operation information, and outputs the command to the command execution unit 306. The command execution unit 306 executes the input command. In this way, the home electronics device 300 appropriately recognizes the contents of the voice spoken by the user using the semantic information table 301.

FIG. 14 is a block diagram of a home electronics system as a second use example of the semantic information table. The home electronic system hands the function of voice recognition over to a server 500 present over cloud and operates a home electronics device 400 through voice.

The home electronics device 400 and the server 500 are connected to each other via a public communication network, such as the Internet.

The home electronics device 400 is identical to the home electronics device 300 described with reference to FIG. 13. In the second example, however, the home electronics device 400 does not perform voice recognition, and the server 500 thus includes a semantic information table 501, a voice processor 502, an analyzer 503, and a command generator 504.

A microphone 401 is identical to the microphone 302 of FIG. 13. A signal processor 402 determines whether the audio signal input from the microphone 401 is noise or not. If the audio signal is not noise, the signal processor 402 outputs the audio signal to a communication unit 404. The communication unit 404 converts the input audio signal into a communication signal in a communicable format, and then transmits the communication signal to the server 500.

A communication unit 505 in the server 500 receives the communication signal from the home electronics device 400, extracts the audio signal, and outputs the audio signal to the voice processor 502. As the voice processor 303 of FIG. 13, the voice processor 502 analyzes the input audio signal, and generates text data indicating the voice spoken by the user. As the analyzer 304 of FIG. 13, the analyzer 503 analyzes the text data generated by the voice processor 502 using the semantic information table 501, and outputs operation information to the command generator 504.

The command generator 504 generates a command to execute an operation indicated by the input operation information, and then outputs the command to the communication unit 505. The communication unit 505 converts the input command into a communication signal in a communicable format, and then transmits the communication signal to the home electronics device 400.

The communication unit 404 in the home electronics device 400 receives the communication signal, removes a header and the like from the received communication signal, and then outputs the resulting communication signal to the signal processor 402. If the communication signal with the header removed therefrom is a command to the home electronics device 400, the signal processor 402 outputs that command to the command execution unit 403. The command execution unit 403 executes the input command.

In the home electronics system of FIG. 14, the server 500 appropriately recognizes the contents of the operation spoken by the user, using the semantic information table 501 that has been generated through the learning process, and then transmits the command to the home electronics device 400.

The word semantic information generation apparatus of the disclosure finds applications in the treatment of the meaning of a natural language text. For example, the word semantic information generation apparatus is applicable to searching for sentences similar in meaning, performing a word interchanging process, or semantically sorting spoken sentences in an interactive system.

What is claimed is:

1. A method for generating, with a processor, semantic information associated with spoken voice in order to control an electronic device, comprising:
   acquiring, with a processor, a first text corpus, including first text data of a first sentence including a first word and described in a natural language, and second text data of a second sentence including a second word different in meaning from the first word, with a second word distribution indicating types and frequencies of words appearing within a predetermined range prior to and subsequent to the second word being similar to a first word distribution within the predetermined range prior to and subsequent to the first word in the first sentence;
   acquiring, with the processor, a second text corpus including third text data of a third sentence, including a third word identical to at least one of the first word and the second word, with a third word distribution within the predetermined range prior to and subsequent to the third word being not similar to the first word distribution;
   in accordance with an arrangement of a word string in the first text corpus and the second text corpus, performing, with the processor, a learning process by assigning to the first word a first vector representing a meaning of the first word in a vector space of predetermined dimensions and by assigning to the second word a second vector representing a meaning of the second word in the vector space;
   storing the first vector in association with the first word, and the second vector spaced by a predetermined distance or longer from the first vector in the vector space in association with the second word; and
   generating, with the processor, a command based on the first vector and the second vector,
   wherein the electronics device is controlled in accordance with the command.

2. The method according to claim 1,
   wherein the second text corpus comprises the third word and a fourth word that is artificially produced and does not appear in text data of the natural language, and
   wherein a word included in the predetermined range prior to and subsequent to the third word is the fourth word in the third text data.

3. The method according to claim 1,
   wherein the first text data and the second text data comprise a word in a first language, and
   wherein in the third text data, the third word is a word in the first language, and a word within the predetermined range prior to and subsequent to the third word is a word in a second language different from the first language.

4. The method according to claim 1,
   wherein the second word is an antonym of the first word.

5. The method according to claim 1,
   wherein the second word is similar in meaning to the first word, but different in terms of a degree of similarity from the first word.

6. The method according to claim 1,
   wherein the second word is identical in concept to the first word, but different in attribute from the first word.

7. The method according to claim 1,
   wherein the learning process is performed using a neural network.

8. The method according to claim 1,
   wherein the learning process is performed using latent semantic indexing.

9. The method according to claim 1,
   wherein the learning process is performed using probabilistic semantic indexing.

10. The method according to claim 1,
    wherein the vector space of the predetermined dimensions has a number of dimensions equal to a number of different types of words appearing in the first text corpus and the second text corpus.

11. The method according to claim 1,
    wherein the first text corpus comprises text data in the natural language that is used to instruct a device to perform an operation, and
    wherein the third word is related to contents of the operation of the device.

12. The method according to claim 1, further comprising:
    receiving audio signal of speech spoken by a user;
    generating text data from the audio signal of the speech spoken by the user; and
    determining and outputting semantic information of each word included in the text data by referencing the first vector that is stored and the second vector that is stored.

13. An apparatus for generating semantic information associated with spoken voice in order to control an electronic device, comprising:
    one or more memories; and circuitry which, in operation executes
    acquiring a first text corpus, including first text data of a first sentence including a first word and described in a natural language, and second text data of a second sentence including a second word different in meaning from the first word, with a second word distribution indicating types and frequencies of words appearing within a predetermined range prior to and subsequent to the second word being similar to a first word distribution within the predetermined range prior to and subsequent to the first word in the first sentence;
    acquiring a second text corpus including third text data of a third sentence, including a third word identical to at least one of the first word and the second word, with a third word distribution within the predetermined range prior to and subsequent to the third word being not similar to the first word distribution;
    performing, in accordance with an arrangement of a word string in the first text corpus and the second text corpus, a learning process by assigning to the first word a first vector representing a meaning of the first word in a vector space of predetermined dimensions and by assigning to the second word a second vector representing a meaning of the second word in the vector space;
    storing the first vector in association with the first word, and the second vector spaced by a predetermined distance or longer from the first vector in the vector space in association with the second word; and
    generating, with the processor, a command based on the first vector and the second vector,
    wherein the electronics device is controlled in accordance with the command.

14. The apparatus according to claim 13, wherein the circuitry, in operation, further executes:
    receiving audio signal of speech spoken by a user;
    generating text data from the audio signal of the speech spoken by the user; and
    determining and outputting semantic information of each word included in the text data by referencing the first vector that is stored and the second vector that is stored.

15. A non-transitory computer-readable recording medium storing a program, the program which, when executed by a processor, causes the processor to perform a process for generating semantic information associated with spoken voice in order to control an electronic device, the process comprising:
    acquiring, with the processor, a first text corpus, including first text data of a first sentence including a first word and described in a natural language, and second text data of a second sentence including a second word different in meaning from the first word, with a second word distribution indicating types and frequencies of words appearing within a predetermined range prior to and subsequent to the second word being similar to a first word distribution within the predetermined range prior to and subsequent to the first word in the first sentence;
    acquiring, with the processor, a second text corpus including third text data of a third sentence, including a third word identical to at least one of the first word and the second word, with a third word distribution within the predetermined range prior to and subsequent to the third word being not similar to the first word distribution;
    in accordance with an arrangement of a word string in the first text corpus and the second text corpus, performing, with the processor, a learning process by assigning to the first word a first vector representing a meaning of the first word in a vector space of predetermined dimensions and by assigning to the second word a second vector representing a meaning of the second word in the vector space;
    storing the first vector in association with the first word, and the second vector spaced by a predetermined distance or longer from the first vector in the vector space in association with the second word; and
    generating, with the processor, a command based on the first vector and the second vector,
    wherein the electronics device is controlled in accordance with the command.

16. The non-transitory computer-readable recording medium according to claim 15, the process further comprising:
    receiving audio signal of speech spoken by a user;
    generating text data from the audio signal of the speech spoken by the user; and
    determining and outputting semantic information of each word included in the text data by referencing the first vector that is stored and the second vector that is stored.

\* \* \* \* \*